(12) United States Patent
Church et al.

(10) Patent No.: US 6,326,489 B1
(45) Date of Patent: Dec. 4, 2001

(54) SURFACE-BOUND, BIMOLECULAR, DOUBLE-STRANDED DNA ARRAYS

(75) Inventors: George M. Church; Martha L. Bulyk, both of Brookline, MA (US)

(73) Assignees: Howard Hughes Medical Institute, Chevy Chase, MD (US); President & Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/906,543

(22) Filed: Aug. 5, 1997

(51) Int. Cl.[7] .............................. C07H 21/00; C12Q 1/68
(52) U.S. Cl. .................................. 536/25.3; 435/6
(58) Field of Search ................... 435/5, 6, 91.2; 536/22.1, 25.3

(56) References Cited

U.S. PATENT DOCUMENTS

| | | | |
|---|---|---|---|
| 4,731,325 | 3/1988 | Palva et al. | 435/6 |
| 5,302,509 | 4/1994 | Cheeseman | 435/6 |
| 5,306,619 | 4/1994 | Edwards et al. | 435/6 |
| 5,324,633 | 6/1994 | Fodor et al. | 435/6 |
| 5,328,825 | 7/1994 | Warren et al. | 435/6 |
| 5,405,746 | 4/1995 | Uhlen | 435/6 |
| 5,424,186 | 6/1995 | Fodor et al. | 435/6 |
| 5,426,180 | 6/1995 | Kool | 536/25.3 |
| 5,437,976 | 8/1995 | Utermohlen | 435/6 |
| 5,445,934 | 8/1995 | Fodor et al. | 435/6 |
| 5,484,702 | 1/1996 | Ludwig | 435/6 |
| 5,510,270 | 4/1996 | Fodor et al. | 436/518 |
| 5,527,681 | 6/1996 | Holmes | 435/6 |
| 5,545,531 | 8/1996 | Rava et al. | 435/6 |
| 5,552,270 | 9/1996 | Khrapko et al. | 435/6 |
| 5,556,752 | 9/1996 | Lockhart et al. | 435/6 |
| 5,571,639 | 11/1996 | Hubbell et al. | 430/5 |
| 5,578,444 | 11/1996 | Edwards et al. | 435/6 |
| 5,578,832 | 11/1996 | Trulson et al. | 250/458.1 |
| 5,587,128 | 12/1996 | Wilding et al. | 422/50 |
| 5,593,839 | 1/1997 | Hubbell et al. | 435/6 |
| 5,599,695 | 2/1997 | Pease et al. | 435/91.1 |
| 5,616,478 | 4/1997 | Chetverin et al. | 435/91.2 |
| 5,631,134 | 5/1997 | Cantor | 435/6 |
| 5,641,658 | 6/1997 | Adams et al. | 435/91.2 |

FOREIGN PATENT DOCUMENTS

| | | |
|---|---|---|
| WO 93/17126 | 9/1993 | (WO) . |
| WO 96/28457 | 9/1996 | (WO) . |
| WO 96/36731 | 11/1996 | (WO) . |
| WO 97/09449 | 3/1997 | (WO) . |
| WO 97/10365 | 3/1997 | (WO) . |

OTHER PUBLICATIONS

Brenner et al., 1992, Encoded combinational chemistry, *Proc. Natl. Acad. Sci. U.S.A.*, 86: 5381–5383.
Lam et al., 1991, A new type of synthetic peptide library for identifying ligand–binding activity, *Nature*, 354: 82–84.
Scott et al., 1990, Searching for Peptide Ligands with an Epitope Library, *Science*, 249: 386–390.
International Search Report for International Application No. PCT/US98/15408, dated Oct. 28, 1998.

*Primary Examiner*—Eggerton A. Campbell
(74) *Attorney, Agent, or Firm*—Banner & Witcoff, Ltd.

(57) ABSTRACT

The invention provides an array of surface-bound, bimolecular, double-stranded, nucleic acid molecules, the array comprising a solid support, and a plurality of different double-stranded nucleic acid molecule members, a member comprising a first nucleic acid strand linked to the solid support and a second nucleic acid strand which is substantially complementary to the first strand and complexed to the first strand by Watson-Crick base pairing, wherein at least a portion of the members have a second nucleic acid strand is substantially complementary to and base paired with the first strand along the entire length of the first strand.

11 Claims, 5 Drawing Sheets

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 16 bases
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 1:

TCCACACTCT CCAACA                                                           16

(2) INFORMATION FOR SEQ ID NO: 2:

(i) SEQUENCE CHARACTERISTICS:
       (A) LENGTH: 16 bases
       (B) TYPE: nucleic acid
       (C) STRANDEDNESS: single
       (D) TOPOLOGY: linear (ii) MOLECULE TYPE: other nucleic acid (xi) SEQUENCE DESCRIPTION: SEQ ID NO: 2:

GGACCCTTTG ACTTGA                                                           16

SURFACE-BOUND, BIMOLECULAR, DOUBLE-STRANDED DNA ARRAYS

BACKGROUND OF THE INVENTION

Compact arrays or libraries of surface-bound, double-stranded oligonucleotides are of use in rapid, high-throughput screening of compounds to identify those that bind, or otherwise interact with, short, double-stranded DNA sequence motifs. Of particular interest are proteins, particularly trans-regulatory factors, that control gene transcription. Ideally, such an oligonucleotide array is bound to the surface of a solid support matrix that is of a size that enables laboratory manipulations, e.g. an incubation of a candidate protein with the nucleic acid targets sequences thereon, and that is itself inert to chemical interactions with experimental proteins, buffers and/or other components. In addition, it is desirable that the absolute number of unique target sequences in the array be maximized, since methods of high-throughput screening are used in the attempt to minimize repetition of steps that are labor-intensive or otherwise costly.

A high-density, double-stranded DNA array complexed to a solid matrix is described by Lockhart (U.S. Pat. No. : 5,556,752); however, the DNA molecules therein disclosed are produced as unimolecular products of chemical synthesis. Each member of the array contains regions of self-complementarity separated by a spacer (i.e. a single-strand loop), such that these regions hybridize to each other in order to produce a double-helical region. A difficulty of such a production method arises when the accuracy of chemical synthesis is considered in light to that of that demonstrated by proteinaceous DNA polymerase molecules. It is estimated that enzymatic synthesis of second-strand DNA from a first-strand template operates at 100-fold higher fidelity than do chemical synthetic procedures. Further, it is required that those regions of complementary nucleic acid sequences that must hybridize in order to form the double-helical structure are physically attached to each other by a linker subunit.

SUMMARY OF THE INVENTION

The present invention encompasses an array of surface-bound, bimolecular, double-stranded, nucleic acid molecules, the array comprising a solid support, and a plurality of different double-stranded nucleic acid molecule members, a member comprising a first nucleic acid strand linked to the solid support and a second nucleic acid strand which is substantially complementary to the first strand and complexed to the first strand by Watson-Crick base pairing, wherein at least a portion of the members have a second nucleic acid strand which is substantially complementary to and base paired with the first strand along the entire length of the first strand.

The term "synthetic", as used herein, is defined as that which is produced by in vitro chemical or enzymatic synthesis. The synthetic arrays of the present invention may be contrasted with natural nucleic acid molecules such as viral or plasmid vectors, for instance, which may be propagated in bacterial, yeast, or other living hosts.

As used herein, the term "nucleic acid" is defined to encompass DNA and RNA or both synthetic and natural origin. The nucleic acid may exist as single- or double-stranded DNA or RNA, an RNA/DNA heteroduplex or an RNA/DNA copolymer, wherein the term "copolymer" refers to a single nucleic acid strand that comprises both ribonucleotides and deoxyribonucleotides.

The phrase "different nucleic acid molecule members" means that the double-stranded nucleic acid molecules attached to the surface include double-stranded nucleic acid molecules of of different nucleotide sequence.

When used herein in this context, the term "double-stranded" refers to a pair of nucleic acid molecules, as defined above, that exist in a hydrogen-bonded, helical array typically associated with DNA, and that under these umbrella terms are included those paired oligonucleotides that are essentially double-stranded, meaning those that contain short regions of mismatch, such as a mono-, di- or tri-nucleotide, resulting from design or error either in chemical synthesis of the oligonucleotide priming site on the first nucleic acid strand or in enzymatic synthesis of the second nucleic acid strand.

As used herein, the terms "complementary" and "substantially complementary" refer to the hybridization or base pairing between nucleotides or nucleic acids, such as, for instance, between the two strands of a double-stranded DNA molecule or between an oligonucleotide primer and a primer binding site on a single stranded nucleic acid to be sequenced or amplified.

Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

As used herein, the term "array" is defined to mean a heterogeneous pool of nucleic acid molecules that is affixed to a substrate or solid support in a manner that permits identification of individual members during the course of experimental manipulation.

According to the invention, the array may have virtually any number of different members. In preferred embodiments, the array comprises from 2 up to 100 members, more preferably from 100 up to 10,000 members and highly preferably from 10,000 up to 1,000,000 members, preferably on a solid support. In preferred embodiments, the array will have a density of more than 100 members at known locations per $cm^2$, preferably more than 1,000 per $cm^2$, more preferably more than 10,000 per $cm^2$.

According to the methods disclosed herein, a "substrate" or "solid support" is defined as any material having a rigid or semi-rigid surface.

It is contemplated that attached to the solid support is a spacer. The spacer molecule is preferably of sufficient length to permit the double-stranded oligonucleotide in the completed member of the array to interact freely with molecules exposed to the array. The spacer molecule, which may comprise as little as a covalent bond length, is typically 6–50 atoms long to provide sufficient exposure for the attached double-stranded DNA molecule. The spacer is comprised of a surface attaching portion and a longer chain portion.

Preferably, the 3' end of the first strand is linked to the solid support.

It is preferred that the 5' end of the first strand and 3' end of the second strand are not linked via a covalent bond, and thus do not form a continuous single strand. As used herein in this context, "covalent bond" is defined as meaning a bond that forms, directly or via a spacer comprising nucleic acid or another material, a continuous strand that comprises the 5' end of the first strand and the 3' end of the second strand, and thus includes a 3'/5' phosphate bond as occurs naturally in a single-stranded nucleic acid. This definition does not encompass intermolecular crosslinking of the first and second strands.

It is additionally preferred that the 5' end of the second strand is not linked to the support.

It is preferred that the solid support is a silica support.

It is also preferred that the first strand is produced by chemical synthesis and that the second strand is produced by enzymatic synthesis.

Preferably, the first strand is used as the template on which the second strand is enzymatically produced.

It is additionally preferred that in each member of the array, the first strand contains at its 3' end a binding site for an oligonucleotide primer which is used to prime enzymatic synthesis of the second strand, and at its 5' end a variable sequence.

An "oligonucleotide primer", as referred to herein, is defined as a single-stranded DNA or RNA molecule that is hybridized to a nucleic acid template to prime enzymatic synthesis of a second nucleic acid strand.

It is preferred that enzymatic synthesis of the second strand is performed using an enzyme. Preferably, the oligonucleotide primer is between 10 and 30 nucleotides in length.

It is preferred that the first strand comprises DNA.

It is additionally preferred that the second strand comprises DNA.

It is preferred that the first and second strands each comprise from 16 to 60 monomers selected from the group that includes ribonucleotides and deoxyribonucleotides.

Use of the term "monomer" is made to indicate any of the set of molecules which can be joined together to form an oligomer or polymer. The set of monomers useful in the present invention includes, but is not restricted to, for the example of oligonucleotide synthesis, the set of nucleotides consisting of adenine, thymine, cytosine, guanine, and uridine (A, T, C, G, and U, respectively) and synthetic analogs thereof. As used herein, "monomer" refers to any member of a basis set for synthesis of an oligomer. Different basis sets of monomers may be used at successive steps in the synthesis of a polymer.

In a particularly preferred embodiment, the solid support is a silica support and the first and second strands each comprise from 16 to 60 monomers selected from the group that includes ribonucleotides and deoxyribonucleotides.

It is also preferred that a chimeric protein comprising a DNA binding domain fused in frame to Green Fluorescent Protein is bound to nucleic acid molecules of said array.

The present invention also provides a method for the construction of a synthetic, surface bound nucleic acid array, comprising the steps of (a) performing chemical synthesis of a first nucleic acid strand that is linked to a solid support, (b) hybridizing to the first strand of step (a) an oligonucleotide primer that is substantially complementary to a sequence comprised by the first strand, and (c) performing enzymatic synthesis of a second nucleic acid strand that is complementary to the first strand of step (a), wherein the second strand is complexed to the first strand by Watson-Crick base pairing.

Preferably, the 3' end of the first strand is linked to the solid support.

It is preferred that the 5' end of the first strand and the 3' end of the second strand are not linked via a covalent bond.

It is additionally preferred that the 5' end of the second strand is not linked to the support.

Preferably, the solid support is a silica support.

It is also preferred that in each member of the array, the first strand contains at its 3' end a binding site for an oligonucleotide primer which is used to prime enzymatic synthesis of the second strand, and at its 5' end a variable sequence.

It is additionally preferred that the enzymatic synthesis of the second strand is performed using an enzyme.

Preferably, the oligonucleotide primer of step (c) is between 10 and 30 nucleotides in length.

In a preferred embodiment, the first strand comprises DNA.

It is additionally preferred that the second strand comprises DNA.

Preferably, the first and second strands each comprise from 16 to 60 monomers selected from the group that includes ribonucleotides and deoxyribonucleotides.

Preferably, the solid support is a silica support. More preferably, the solid support is a silica support and the first and second strands each comprise from 16 to 60 monomers selected from the group that includes ribonucleotides and deoxyribonucleotides.

The invention provides an improvement over know nucleic acid arrays or libraries in that while the first strand of the DNA duplex is chemically-synthesized on the support matrix, the second strand is enzymatically produced using the first strand as a template. While the error rate in production of the first strand remains the same, increased fidelity of second strand synthesis is expected, consequently, to result in a higher percentage of points on the matrix surface that are filled by hybridized DNA duplex molecules that can serve as targets for binding- or other assays. In addition, oligonucleotide priming of second strand synthesis obviates the need for covalent linkage of complementary regions, with the effect of reducing extraneous sequence or non-nucleic acid material from the array, as well as eliminating steps of designing and synthesizing such a linker.

Further features and advantages of the invention will become more fully apparent in the following description of the embodiments and drawings thereof, and from the claims.

DESCRIPTION

Figure 1:
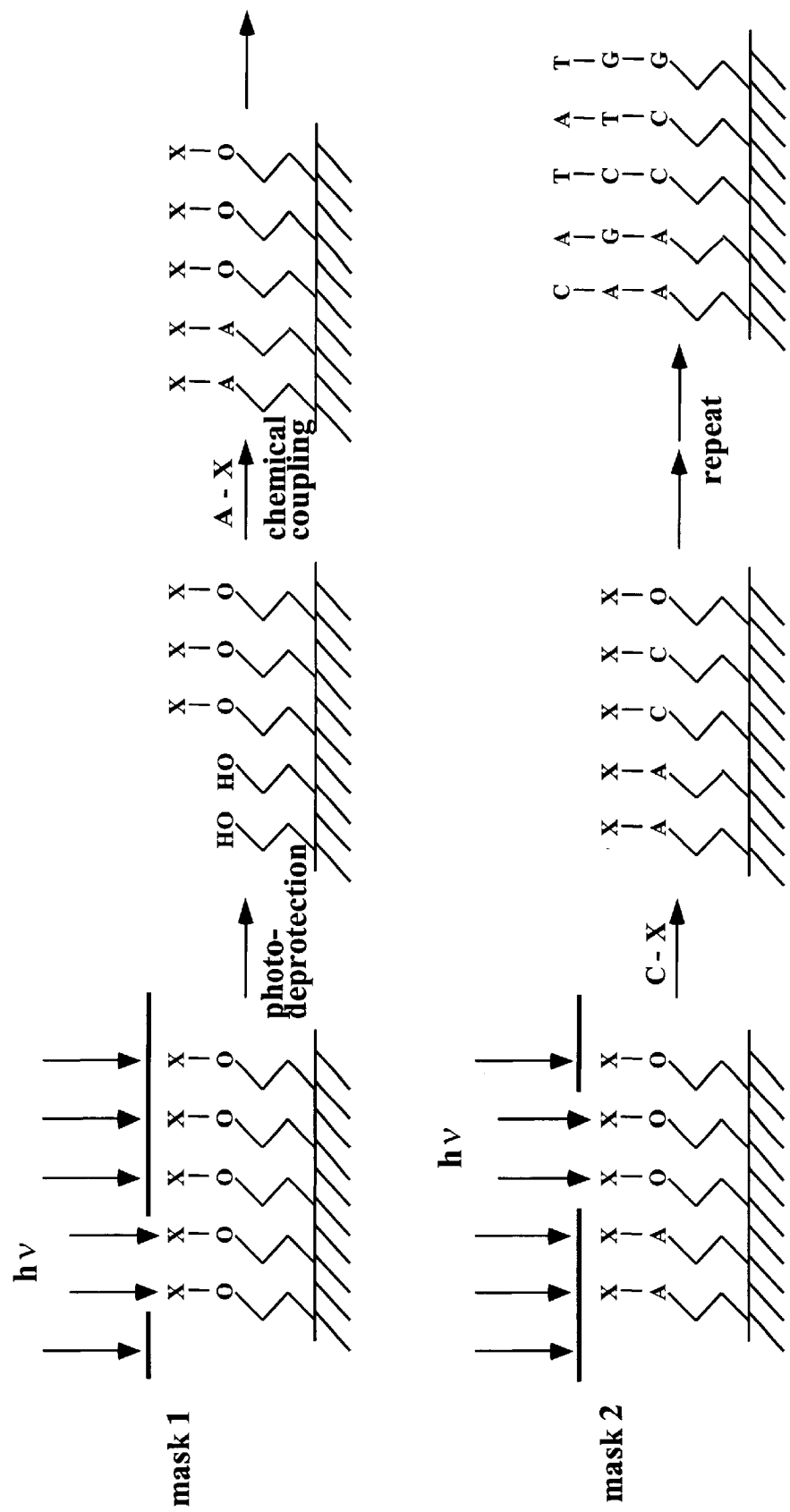
FIG. 1 presents a schematic summary of light-directed DNA synthesis.

Bimolecular Double-Stranded Arrays According To The Invention

The invention is based on the recognition that bimolecular double-stranded nucleic acid molecule arrays may be provided, and that such arrays possess the advantage of a high fidelity of second strand synthesis, and are therefore provide an array of true duplex nucleic acid. Described below is how to prepare an array of immobilized first strand, how to prepare and/or design a primer useful according to the invention, and how to primer synthesis of a second strand that is complementary to and duplexed with the first array-bound strand.

Preparation of Array of Immobilized First DNA Strand

Synthesis of the nucleic acid arrays of the present invention is a bipartite process, which entails the production of a diverse array of single-stranded DNA molecules that are immobilized on a the surface of a solid support matrix, followed by priming and enzymatic synthesis of a second nucleic acid strand, either RNA or DNA. A highly preferred method of carrying out synthesis of the immobilized single-stranded array is that of Lockhart, described in U.S. Pat. No. 5,556,752 the contents of which are herein incorporated by reference. Of the methods described therein, that which is of particular use describes synthesis of such an array on the surface of a single solid support has a plurality of preselected regions. A method whereby each chemically distinct member of the array is synthesized on a separate solid support is also described by Lockhart. These methods, and others, are briefly summarized below.

The solid support may comprise biological, nonbiological, organic or inorganic materials, or a combination of any of these. It is contemplated that such materials may exist as particles, strands, precipitates, gels, sheets, tubing, spheres, containers, capillaries, pads, slices, films, plates or slides. Preferably the solid support takes the form of plates or slides, small beads, pellets, disks or other convenient forms. It is highly preferred that at least one surface of the substrate will be substantially flat. The solid support may take on alternative surface configurations. For example, the solid support may contain raised or depressed regions on which synthesis takes place. In some instances, the solid support will be chosen to provide appropriate light-absorbing characteristics. For example, the support may be a polymerized Langmuir Blodgett film, functionalized glass, Si, Ge, GaAs, GaP, SiO2, SiN4, modified silicon, or any one of a variety of gels or polymers such as (poly)tetrafluoroethylene, (poly)vinylidendifluoride, polystyrene, polycarbonate, or combinations thereof. Other suitable solid support materials may be used, and will be readily apparent to those of skill in the art. Preferably, the surface of the solid support will contain reactive groups, which could be carboxyl, amino, hydroxyl, thiol, or the like. More preferably, the surface will be optically transparent and will have surface Si—OH functionalities, such as are found on silica surfaces.

According to the invention, a first nucleic acid strand is anchored to the solid support by as little as an intermolecular covalent bond. Alternatively, a more elaborate linking molecule may attach the nucleic acid strand to the support. Such a molecular tether may comprise a surface-attaching portion which is directly attached to the solid support. This portion can be bound to the solid support via carbon-carbon bonds using, for example, supports having (poly) trifluorochloroethylene surfaces, or preferably, by siloxane bonds (using, for example, glass or silicon oxide as the solid support). Siloxane bonds with the surface of the support can be formed via reactions of surface attaching portions bearing trichlorosily1 or trialkoxysily1 groups. The surface attaching groups will also have a site for attachment of the longer chain portion. It is contemplated that suitable attachment groups may include amines, hydroxyl, thiol, and carboxyl groups. Preferred surface attaching portions include aminoalkylsilanes and hydroxyalkylsilanes. It is particularly preferred that the surface attaching portion of the spacer is selected from the group comprising bis(2-hydroxyethyl)-aminopropyltriethoxysilane, 2-hydroxyethylaminopropyltriethoxysilane, aminopropyltriethoxysilane and hydroxypropyltriethoxysilane.

The longer chain portion of the spacer can be any of a variety of molecules which are inert to the subsequent conditions for polymer synthesis, examples of which include: aryl acetylene, ethylene glycol oligomers containing 2–14 monomer units, diamines, diacids, amino acids, peptides, or combinations thereof. It is contemplated that the longer chain portion is a polynucleotide. The longer chain portion which is to be used as part of the spacer can be selected based upon its hydrophilic/hydrophobic properties to improve presentation of the double-stranded oligonucleotides to certain receptors, proteins or drugs. It can be constructed of polyethyleneglycols, polynucleotides, alkylene, polyalcohol, polyester, polyamine, polyphosphodiester and combinations thereof.

Additionally, for use in synthesis of the arrays of the invention, the spacer will typically have a protecting group, attached to a functional group (i.e., hydroxyl, amino or carboxylic acid) on the distal or terminal end of the chain portion (opposite the solid support). After deprotection and coupling, the distal end is covalently bound to an oligomer.

As used in discussion of the spacer region, the term "alkyl" refers to a saturated hydrocarbon radical which may be straight-chain or branced-chain (for example, ethyl, isopropyl, t-amyl, or 2,5-0dimethylhexyl). When "alkyl" or "alkylene" is used to refer to a linking group or a spacer, it is taken to be a group having two available valences for covalent attachment, for example, $—CH_2CH_2—$, $—CH_2CH_2CH_2—$, $—CH_2CH_2CH(CH_3)CH_2——CH_2(CH_2CH_2)_2CH_2—$. Preferred alkyl groups as substitutents are those containing 1 to 10 carbon atoms, with those containing 1 ato 6 carbon atoms being particularly preferred. Preferred alkyl or alkylene groups as linking groups are those containing 1 to 20 carbon atoms, with those containing 3 to 6 carbon atoms being particularly preferred. The term "polyethylene glycol" is used to refer to those molecules which have repeating units of ethylene glycol, for example, hexaethylene glycol $(HO—(CH_2CH_2O)_5—CH_2(CH_2CH_2OH)$. When the term "polyethylene glycol" is used to refer to linking groups and spacer groups, it would be understood by one of skill in the art that other polyethers of polyols could be used as well (i.e., polypropylene glycol or mixtures of ethylene and propeylene glycols).

The term "protecting group", as used herein, refers to any of the groups which are designed to block one reactive site in a molecule while a chemical reaction is carried out at another reactive site. More particularly, the protecting groups used herein can be any of those groups described in Greene et al., 1991, *Protective Groups In Organic Chemistry*, 2nd Ed., John Wiley & Sons, New York, N.Y, incorporated herein by reference. The proper selection of protecting groups for a particular synthesis will be governed by the overall methods employed in the synthesis. For example, in "light-directed" synthesis, discussed below, the protecting groups will be photolabile protecting groups, e.g. NVOC and MeNPOC. In other methods, protecting groups may be removed by chemical methods and include groups such as FMOC, DMT and others known to those of skill in the art.

Nucleic Acid Arrays on a Single Substrate

1. Light-directed methods

Where a single solid support is employed, the oligonucleotides of the present invention can be formed using a variety of techniques known to those skilled in the art of polymer synthesis on solid supports. For example, "light-directed" methods, techniques in a family of methods known as VLSIPS™ methods, are described in U.S. Pat. No. 5,143,854 and U.S. Pat. No. 5,510,270 and U.S. Pat. No. 5,527,681, which are herein incorporated by reference. These methods, which are illustrated in FIG. 1 (adapted from Pease et al., 1994, *Proc. Natl. Acad. Sci. U.S.A.*, 91: 5022–5026), involve activating predefined regions of a substrate or solid support and then contacting the substrate with a preselected monomer solution. These regions can be activated with a light source, typically shown through a mask (much in the manner of photolithography techniques used in integrated circuit fabrication). Other regions of the substrate remain inactive because illumination is blocked by the mask and they remain chemically protected. Thus, a light pattern defines which regions of the substrate react with a given monomer. By repeatedly activating different sets of predefined regions and contacting different monomer solutions with the substrate, a diverse array of polymers is produced on the substrate. Other steps, such as washing unreacted monomer solution from the substrate, can be used as necessary. Other applicable methods include mechanical techniques such as those described in PCT No. 92/10183, U.S. Pat. No. 5,384,261 also incorporated herein by reference for all purposes. Still further techniques include bead based techniques such as those described in PCT US/93/04145, also incorporated herein by reference, and pin based methods such as those described in U.S. Pat. No. 5,288,514, also incorporated herein by reference.

The VLSIPS™ methods are preferred for making the compounds and arrays of the present invention. The surface of a solid support, optionally modified with spacers having photolabile protecting groups such as NVOC and MeNPOC, is illuminated through a photolithographic mask, yielding reactive groups (typically hydroxyl groups) in the illuminated regions. A 3'-O-phosphoramidite activated deoxynucleoside (protected at the 5'-hydroxyl with a photolabile protecting group) is then presented to the surface and chemical coupling occurs at sites that were exposed to light. Following capping and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of oligonucleotides is produced. Alternatively, an oligomer of from, for example, 4 to 30 nucleotides can be added to each of the preselected regions rather than synthesize each member in one nucleotide monomer at a time.

2. Flow Channel or Spotting Methods

Additional methods applicable to array synthesis on a single substrate are described in U.S. Pat. No. 5,384,261, incorporated herein by reference for all purposes. In the methods disclosed in these applications, reagents are delivered to the substrate by either (1) flowing within a channel defined on predefined regions or (2) "spotting" on predefined regions. Other approaches, as well as combinations of spotting and flowing, may be employed as well. In each instance, certain activated regions of the substrate are mechanically separated from other regions when the monomer solutions are delivered to the various reaction sites.

A typical "flow channel" method applied to arrays of the present invention can generally be described as follows: Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and arrays of the present invention can be implemented in much the same manner. A first monomer, A, can be delivered to and coupled with a first group of reaction regions which have been appropriately activated. Thereafter, a second monomer, B, can be delivered to and reacted with a second group of activated reaction regions. Unlike the flow channel embodiments described above, reactants are delivered in relatively small quantities by directly depositing them in selected regions. In some steps, the entire substrate surface can be sprayed or otherwise coated with a solution, if it is more efficient to do so. Precisely measured aliquots of monomer solutions may be deposited dropwise by a dispenser that moves from region to region. Typical dispensers include a micropipette to deliver the monomer solution to the substrate and a robotic system to control the position of the micropipette with respect to the substrate, or an ink-jet printer. In other embodiments, the dispenser includes a series of tubes, a manifold, an array of pipettes, or the like so that various reagents can be delivered to the reaction regions simultaneously.

3. Pin-Based Methods

Another method which is useful for the preparation of the immobilized arrays of single-stranded DNA molecules X of the present invention involves "pin-based synthesis." This method, which is described in detail in U.S. Pat. No. 5,288,514, previously incorporated herein by reference, utilizes a substrate having a plurality of pins or other extensions. The pins are each inserted simultaneously into individual reagent containers in a tray. An array of 96 pins is commonly utilized with a 96-container tray, such as a 96-well microtitre dish.

Each tray is filled with a particular reagent for coupling in a particular chemical reaction on an individual pin. Accordingly, the trays will often contain different reagents. Since the chemical reactions have been optimized such that each of the reactions can be performed under a relatively similar set of reaction conditions, it becomes possible to conduct multiple chemical coupling steps simultaneously. The invention provides for the use of substrate(s) on which the chemical coupling steps are conducted. The substrate is optionally provided with a spacer, S, having active sites. In the particular case of oligonucleotides, for example, the spacer may be selected from a wide variety of molecules which can be used in organic environments associated with synthesis as well as aqueous environments associated with binding studies such as may be conducted between the nucleic acid members of the array and other molecules. These molecules include, but are not limited to, proteins (or fragments thereof), lipids, carbohydrates, proteoglycans and nucleic acid molecules. Examples of suitable spacers are polyethyleneglycols, dicarboxylic acids, polyamines and alkylenes, substituted with, for example, methoxy and ethoxy groups. Additionally, the spacers will have an active site on the distal end. The active sites are optionally protected initially by protecting groups. Among a wide variety of protecting groups which are useful are FMOC, BOC, t-butyl esters, t-butyl ethers, and the like.

Various exemplary protecting groups are described in, for example, Atherton et al., 1989, *Solid Phase Peptide Synthesis*, IRL Press, incorporated herein by reference. In some embodiments, the spacer may provide for a cleavable function by way of, for example, exposure to acid or base.

Arrays on Multiple Substrates

Yet another method which is useful for synthesis of compounds and arrays of the present invention involves "bead based synthesis." A general approach for bead based synthesis is described in PCT/US93/04145 (filed Apr. 28, 1993), the disclosure of which is incorporated herein by reference.

For the synthesis of molecules such as oligonucleotides on beads, a large plurality of beads are suspended in a suitable carrier (such as water) in a container. The beads are provided with optional spacer molecules having an active site to which is complexed, optionally, a protecting group.

At each step of the synthesis, the beads are divided for coupling into a plurality of containers. After the nascent oligonucleotide chains are deprotected, a different monomer solution is added to each container, so that on all beads in a given container, the same nucleotide addition reaction occurs. The beads are then washed of excess reagents, pooled in a single container, mixed and re-distributed into another plurality of containers in preparation for the next round of synthesis. It should be noted that by virtue of the large number of beads utilized at the outset, there will similarly be a large number of beads randomly dispersed in the container, each having a unique oligonucleotide sequence synthesized on a surface thereof after numerous rounds of randomized addition of bases. As pointed out by Lockhart (U.S. Pat. No. 5,556,752) an individual bead may be tagged with a sequence which is unique to the double-stranded oligonucleotide thereon, to allow for identification during use.

Preparation Of Oligonucleotide Primers Useful In The Invention

Oligonucleotide primers useful according to the invention are single-stranded DNA or RNA molecules that are hybridizable to a nucleic acid template to prime enzymatic synthesis of a second nucleic acid strand. The primer may therefore be of any sequence composition or length, provided it is complementary to a portion of the first strand.

It is contemplated that such a molecule is prepared by synthetic methods, either chemical or enzymatic. Alternatively, such a molecule or a fragment thereof may be naturally occurring, and may be isolated from its natural source or purchased from a commercial supplier. It is contemplated that oligonucleotide primers employed in the present invention will be 6 to 100 nucleotides in length, preferably from 10 to 30 nucleotides, although oligonucleotides of different length may be appropriate.

Additional considerations with respect to design of a selected primer useful according to the invention relate to duplex formation, and are described in detail in the following section.

Oligonucleotide Primer Hybridization To Single-stranded Nucleic Acid Sequences And Extension to Form Bimolecular Double-Stranded Nucleic Acids Of central importance in carrying out the method of the present invention is selective hybridization of an oligonucleotide primer to the first nucleic acid strand in order to permit enzymatic synthesis of the second nucleic acid strand. Any of a number of enzymes well known in the art can be utilized in the synthesis reaction. Preferably, enzymatic synthesis of the second strand is performed using an enzyme selected from the group comprising DNA polymerase I (exo($^-$) Klenow fragment), T4 DNA polymerase, T7 DNA polymerase, modified T7 DNA polymerase, Taq DNA polymerase, exo($^-$) vent DNA polymerase, exo($^-$) deep vent DNA polymerase, reverse transcriptase and RNA polymerase.

Typically, selective hybridization will occur when two nucleic acid sequences are substantially complementary (typically, at least about 65% complementary over a stretch of at least 14 to 25 nucleotides, preferably at least about 75%, more preferably at least about 90% complementary). See Kanehisa, M., 1984, *Nucleic Acids Res.* 12: 203, incorporated herein by reference. As a result, it is expected that a certain degree of mismatch at the priming site can be tolerated. Such mismatch may be small, such as a mono-, di-, or tri-nucleotide. Alternatively, it may encompass loops, which we define as regions in which mismatch encompasses an uninterrupted series of four or more nucleotides. Note that such loops within the oligonucleotide priming site are encompassed by the present invention; however, the invention does not provide double-stranded nucleic acids that comprise loop structures between the 5' end of the first strand and the 3' end of the second strand. In addition, loop structures outside the priming site, but which do not encumber the 5' end of the first strand or the 3' end of the second strand are not provided by the present invention, since there is no known mechanism for generating such structures in the course of enzymatic second-strand nucleic acid synthesis. Both the 5' end of the first strand and the 3' end of the second strand must be free of attachment to each other via a continuous single strand.

Either strand may comprise RNA or DNA. Overall, five factors influence the efficiency and selectivity of hybridization of the primer to the immobilized first strand. These factors are (i) primer length, (ii) the nucleotide sequence and/or composition, (iii) hybridization temperature, (iv) buffer chemistry and (v) the potential for steric hindrance in the region to which the probe is required to hybridize.

There is a positive correlation between primer length and both the efficiency and accuracy with which a primer will anneal to a target sequence; longer sequences have a higher $T_M$ than do shorter ones, and are less likely to be repeated within a given first nucleic acid strand, thereby cutting down on promiscuous hybridization. Primer sequences with a high G-C content or that comprise palindromic sequences tend to self-hybridize, as do their intended target sites, since unimolecular, rather than bimolecular, hybridization kinetics are genererally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a hybridization mixture, while increases in salt concentration facilitate binding. Under stringent hybridization conditions, longer probes must be used, while shorter ones will suffice under more permissive conditions. Stringent hybridization conditions will typically include salt concentrations of less than about 1M, more usually less than about 500 mM and preferably less than about 200 mM.

Hybridization temperatures can be as low as 5° C., but are typically greater than 22° C., more typically greater than about 30° C., and preferably in excess of about 37° C. Longer fragments may require higher hybridization temperatures for specific hybridization. As several factors may affect the stringency of hybridization, the combination of parameters is more important than the absolute measure of any one alone.

Primers must be designed with the above first four considerations in mind. While estimates of the relative merits of numerous sequences can be made mentally, computer programs have been designed to assist in the evaluation of these several parameters and the optimization of primer sequences. Examples of such programs are "PrimerSelect" of DNAStar and OLIGO™. Once designed, suitable oligonucleotides may be prepared by the phosphoramidite method described by Beaucage and Carruthers, 1981, *Tetrahedron Lett.*, 22: 1859–1862, or by the triester method according to Matteucci et al., 1981, *J. Am. Chem. Soc.*, 103: 3185, both incorporated herein by reference, or by other chemical methods using either a commercial automated oligonucleotide synthesizer or VLSIPST™ technology (discussed in detail below).

The fifth consideration, steric hindrance, is one that was of particular relevance to the development of the invention disclosed herein. While methods for the primed, enzymatic synthesis of second nucleic acid strands from immobilized first strands are known in the art (see Uhlen, U.S. Pat. No. 5,405,746 and Utermohlen, U.S. Pat. No. 5,437,976), the present method differs in that the priming site, as determined by the location of the 3' end of the first strand (X), is adjacent to the surface of the solid support. In a typical silica-based chip array, made as per Lockhart (U.S. Pat. No. 5,556,752), a 20 $\mu m^2$ region carries approximates $4 \times 10^6$ functional copies of a specific sequence, with an intermolecular spacing distance of about 100 Å (Chee et al., 1996, *Science*, 274: 610–614). As a result, it is necessary that the oligonucleotide primer hybridize efficiently to an anchored target in a confined space, and that synthesis proceed outward from the support. In the above-referenced disclosures, it is the 5' end of the first oligonucleotide strand which is linked to the matrix; therefore, priming of the free end of that molecule is permitted, and second-strand extension proceeds toward the solid support. Under the circumstances, significant uncertainty existed as to whether oligonucleotide priming of the end of the first strand proximal to the solid support would occur at a sufficiently high frequency to yield a high-density double-stranded nucleic acid array. The surprising success of this method is described below in Example 1.

EXAMPLE 1

This example illustrates the general synthesis of an array of bimolecular, double-stranded oligonucleotides on a solid support.

Figure 2:
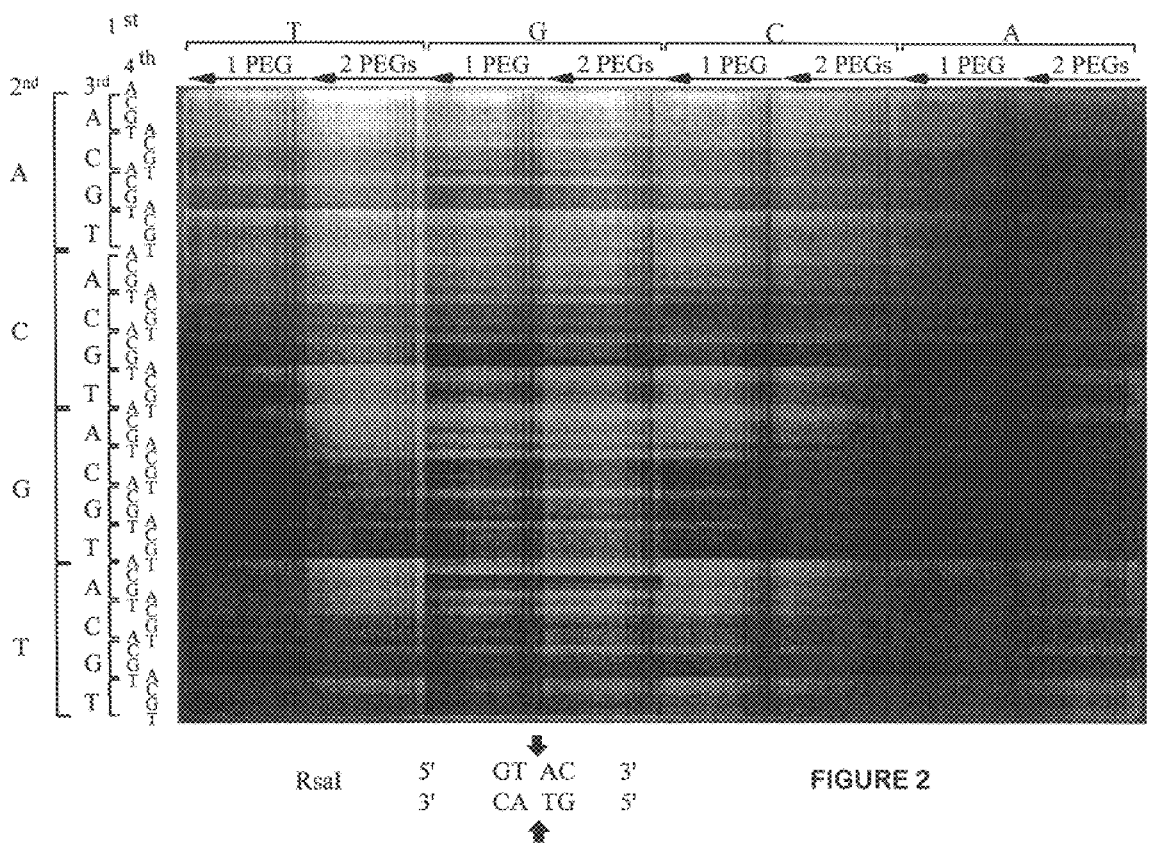
FIG. 2 presents a photomicrograph of a fluorescently-labeled array of bimolecular, double-stranded DNA molecules on a silica chip.

As a first step, single-stranded DNA molecules were synthesized on a solid support using standard light-directed methods (VLSIPST™ protocols), as as described above, using the method of Lockhart, U.S. Pat. No. 5,556,752, the contents of which incoporated above by reference. Hexaethylene glycol (PEG) linkers were used to covalently attach the synthesized oligonucleotides to the derivatized glass surface. A heterogeneous array of linkers was formed such that some sectors of the silica chip had linkers comprising two PEG linkers, while other sectors bore linkers comprising a single PEG molecule (FIG. 2). In addition, the intermolecular distance between linker molecules (and, consequently, nascent nucleic acid strands) was varied such that for either length of linker and for each of the 9,600 distinct molecular species synthesized, were 15 different chip sectors representing the following range of strand densities. These densities, expressed as the percent of total anchoring sites occupied by nucleic acid molecules, are shown in Table 1.

TABLE 1

| % of sites filled |
|---|
| 0.4 |
| 1.6 |
| 3.1 |
| 6.2 |
| 12.5 |
| 25.0 |
| 31.5 |
| 39.7 |
| 50.0 |
| 63.0 |
| 69.1 |
| 75.8 |
| 83.1 |
| 91.2 |
| 100.0 |

Synthesis of the first strand proceeded one nucleotide at a time using repeated cycles of photo-deprotection and chemical coupling of protected nucleotides. The nucleotides each had a protecting group on the base portion of the monomer as well as a photolabile MeNPoc protecting group on the 5' hydroxyl. Note that each of the different molecular species occupies a different physical region on the chip so that there is a one-to-one correspondence between molecular identity and physical location. Moving outward from the chip, the sequence of each molecule proceeds from its 3' to its 5' end (the 3' end of the DNA molecule is attached to the solid surface via a silyl group and 2 PEG linkers), as is the case when chemical synthetic methods are utilized.

Second strand synthesis, as stated above, requires priming of a site at the 3' end of the first nucleic acid strand, followed by enzymatic extension of the primed sequence. DNA polymerase I (exo(⁻) Klenow fragment) was employed in this experiment, although numerous other enzymes, as discussed above, may be advantageously employed. This particular enzyme is optimally active at 37° C.; therefore, two priming sites and the corresponding complementary primers were designed that were predicted to bind efficiently and yet exhibit a minimum of secondary structure at that temperature according to calculations performed by the DNAStar "PrimerSelect" computer program, which was employed for this purpose. The sequences of these primers are as follows:

```
1s 5'-TCCACACTCTCCAACA-3'  (estimated T_M = 36.8° C.)[SEQ ID NO: 1]

2s 5'-GGACCCTTTGACTTGA-3'  (estimated T_M = 38.7° C.)[SEQ ID NO: 2]
```

Note that the optimal reaction temperature varies considerably among polymerases. Also of use according to the methods of the invention are exo(⁻) vent DNA polymerase and exo(−) deep vent DNA polymerase (both commercially available from New England Biolabs, Beverly, Mass.), which are optimally active at 72° C. and approximately 30% active at 50° C., according to the manufacturer. Were these enzymes to be used, longer primer sequences, or those with a higher G-C content, would have to be employed.

In the case of the synthesis presented in FIG. 2, primer S1 [SEQ ID NO: 1] was used. The reaction conditions were as follows:

Prehybridization of chip: 0.005% Triton X-100, 0.2 mg/ml acetylated bovine serum albumin (BSA), 10 mM Tris-HCl (pH 7.5), mM MgCl$_2$ and 7.5 mM dithiothreitol (DTT) at 37° C. for 30 to 60 minutes on a rotisserie.

Second-strand primer extension and fluorescein labeling: 0.005% Triton, 10 mM Tris-HCl (pH 7.5), 5 mM MgCl$_2$, 7.5 mM DTT, 0.4 μmM dNTP's, 0.4 μM primer, 0.04 U/μl DNA Polymerase I (3' to 5' exo(⁻) Klenow fragment, New England Biolabs, Beverly, Mass. ) and 0.0004 mM of fluorescein-12-labeled dATP at 37° C. on a for 1 to 2 hours on a rotisserie, followed by a wash in 0.005% Triton X-100 in 6×SSPE at room temperature. (Note that an alternate labeling procedure, not used in the experiment presented in this Example, is one in which unlabeled extension is performed, followed by labeled primer extension using terminal deoxynucleotide transferase. This reaction takes place as follows: 0.005% Triton X-100, 10 mM Tris acetate, pH 7.5, 10 mM magnesium acetate, 50 mM potassium acetate, 0.044 U/μl terminal transferase and 0.014 mM of any fluorescein-12-labeled dideoxynucleotide at 37° C. for 1–2 hr. on a rotisserie, followed by a wash in 0.005% Triton X-100 in 6×SSPE at room temperature.)

Figure 3:
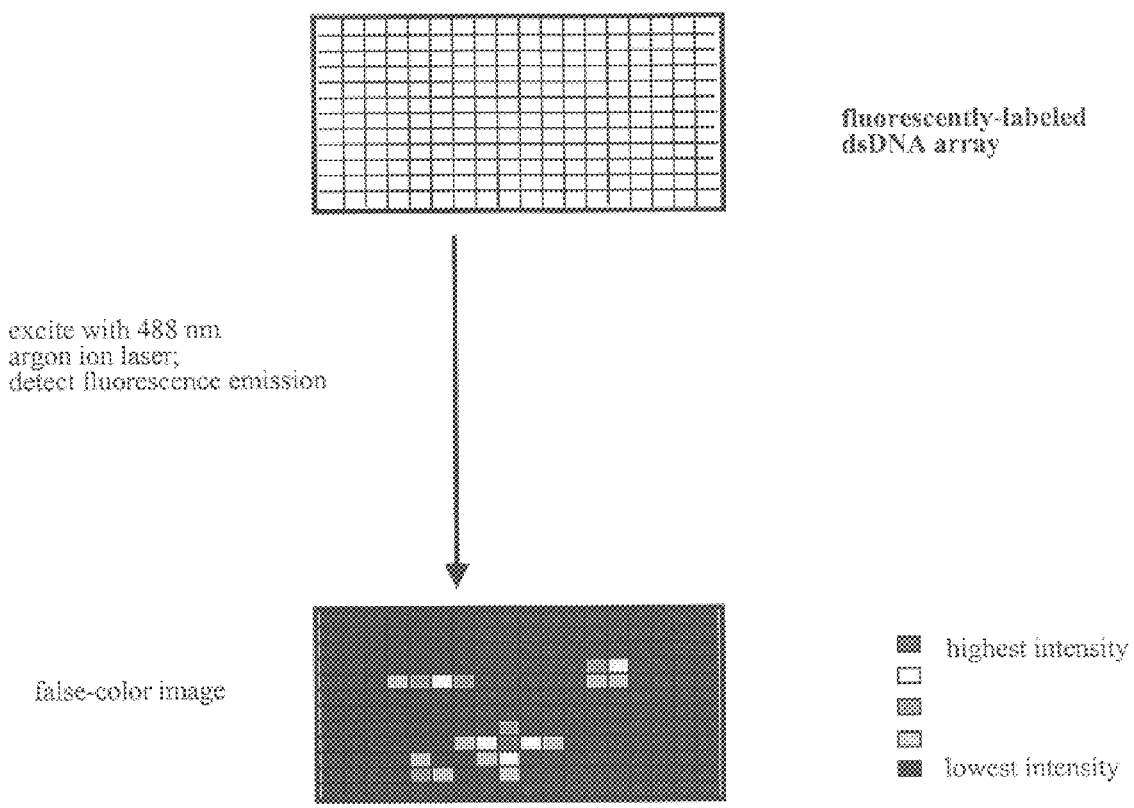
FIG. 3 presents confocal argon laser scanning to detect fluorescently-labeled, surface-bound nucleic acid molecules.

To confirm that second-strand synthesis had taken place, the chip was scanned under a layer of wash buffer for fluorescence in an argon laser confocal scanner (see U.S. Pat. No. 5,578,832). This device exposes the molecules of the array to irradiation at a wavelength of 488 nanometers, which excites electrons in the fluorescein moiety, resulting in fluorescent emissions, which are then recorded at each position of the chip (FIG. 3). Since the first strand was unlabeled, the efficiency of second-strand synthesis can be measured. The result is shown in FIG. 2, where various sectors of the chip fluoresce with different intensities, in proportion both to strand density and to the proportion of dATP residues in the second strand.

Figure 4:
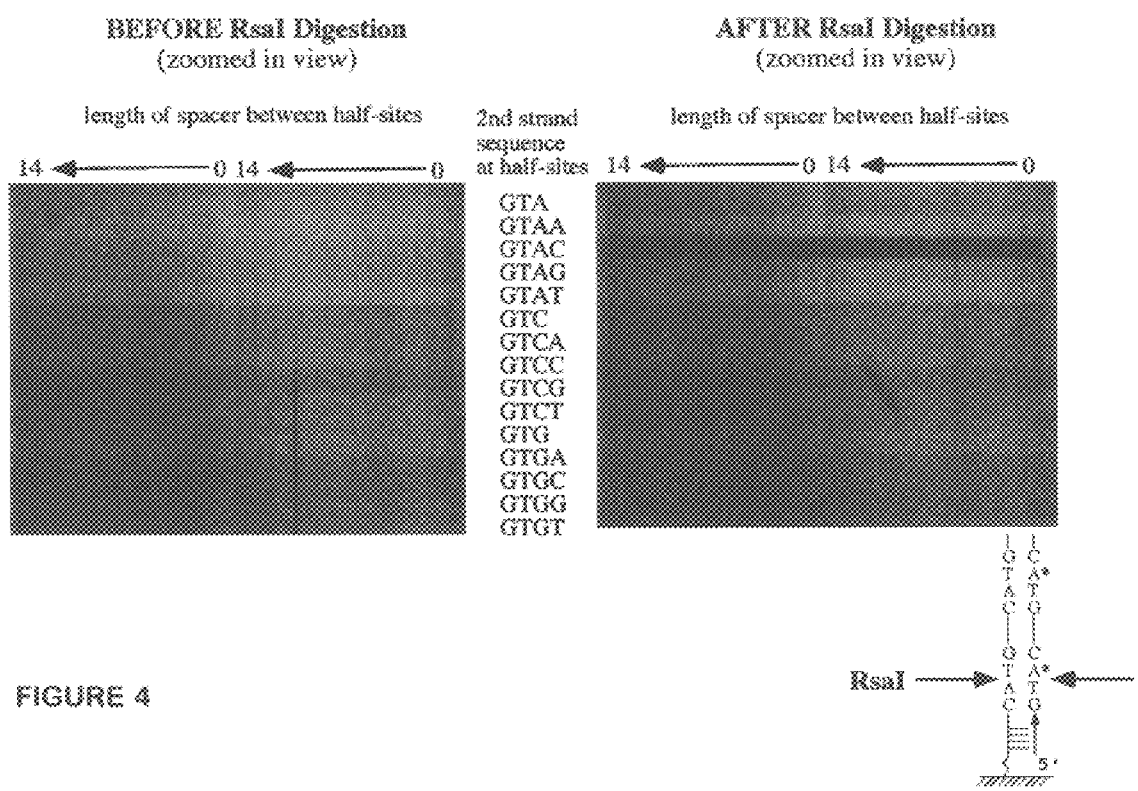
FIG. 4 presents RsaI digestion of a fluorescently-labeled array of bimolecular, double-stranded DNA molecules on a silica chip.

Further confirmation of successful second-strand synthesis was gained from a biochemical assay of the chip. According to the first-strand synthesis procedure, several sectors of the chip were designed such that the several unique sequences synthesized at those positions contained a 4 base motif which, when double-stranded, would form an endonuclease recognition site for the enzyme RsaI. The chip was digested in RsaI, using the manufacturer's recommended incubation conditions. Upon re-scanning of the chip in the argon laser scanner, a dark area appeared. This can be seen in FIG. 2, and is shown in detail in FIG. 4. Since the ability of the enzyme to cleave the sequence from the chip is dependent upon the sequence being double-stranded, synthesis, at least to the point of the recognition site, must have occurred.

Figure 5:
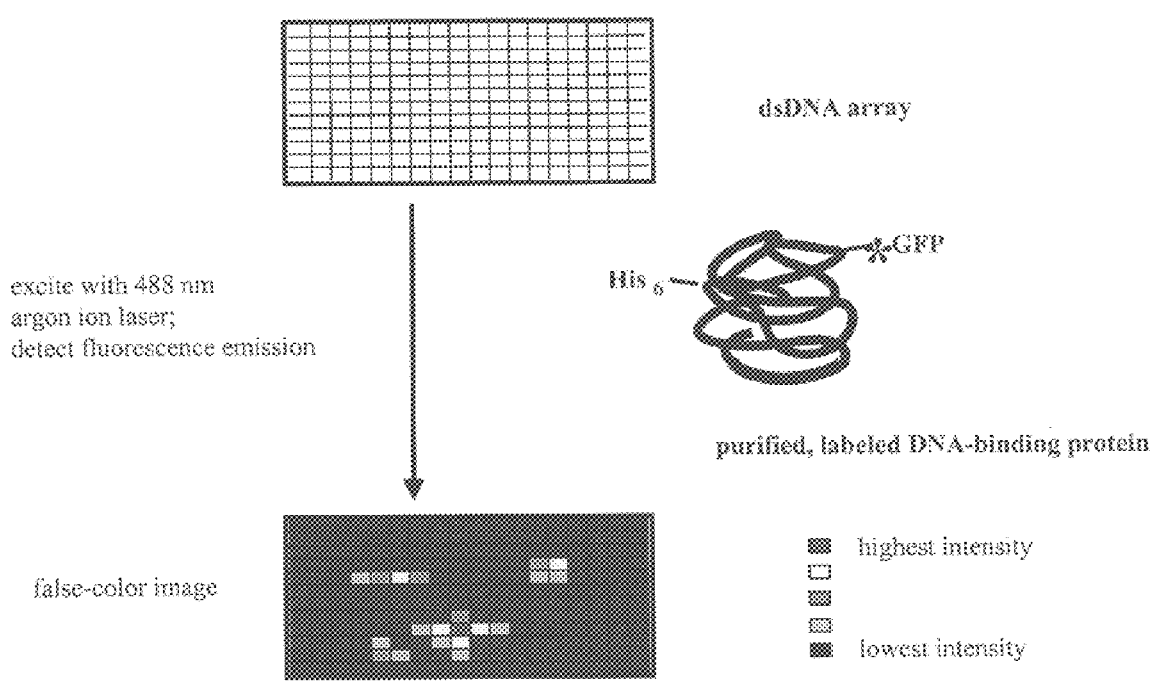
FIG. 5 presents binding of Green Fluorescent Protein to an array of bimolecular, double-stranded DNA molecules on a silica chip, and confocal argon laser scanning to detect the bound protein.

In addition to providing evidence of successful second-strand synthesis, cleavage of double-stranded nucleic acid molecules from the solid support with RsaI demonstrates that members of the array are accessible to proteins in solution, a requirement if the arrays of the invention are to be useful in carrying out assays of protein/DNA interactions. We have devised a procedure in which chimeric proteins, each comprising a DNA binding domain fused in-frame to Green Fluorescent Protein (GFP), are incubated with arrays produced according to the methods of the invention in order to determine a consensus sequence for a given protein/DNA binding motif. After washing away any unbound fusion protein, the support bearing the array is scanned with the confocal argon laser (FIG. 5); the intensity of fluorescence, which is proportional to the amount of protein bound, is correlated with the sequences of nucleic acid molecules, which are known at each position of the scanned surface. The range of sequences to which a protein will bind, as well as the relative efficiency of binding to each, can then be determined. In order to interpret the results, the only source of fluorescence on the chip must be GFP; therefore, the nucleic acid molecules of the array must be unlabeled. The strand extension reaction described above can, if desired, be performed without the use of a fluorescent label; the reaction conditions are identical except that the fluorescein-labeled dATP is omitted, along with the wash step, the purpose of which is to remove unincorporated background fluorescence that ordinarily might interfere with scanning.

USE

The present invention is useful for the production of accurate, high-density arrays of double-stranded nucleic acid molecules the sequences of which can be determined based upon physical location within the array. The arrays provided are, themselves, useful as substrates for multiplex screening of compounds that might physically interact with such nucleic acid sequences, such as DNA binding proteins or other compositions that are of potential scientific or clinical interest, particularly those with therapeutic potential.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method for the construction of a synthetic, surface-bound nucleic acid array, comprising the steps of
   (a) providing a first nucleic acid strand that is linked to a solid support via its 3' end,
   (b) hybridizing to said first strand of step (a) an oligonucleotide primer that is substantially complementary to a sequence comprised by said first strand, and
   (c) performing enzymatic synthesis of a second nucleic acid strand that is complementary to said first strand of step (a), wherein said second strand is complexed to said first strand by Watson-Crick base pairing.

2. The method according to claim 1, wherein the 5' end of said first strand and the 3' end of said second strand are not linked via a covalent bond.

3. The method according to claim 1, wherein the 5' end of said second strand is not linked to said solid support.

4. The method according to claim 1, wherein said solid support is a silica support.

5. The method according to claim 1, wherein said first strand of each member of said array contains at its 3' end a binding site for an oligonucleotide primer which is used to prime enzymatic synthesis of said second, and at its 5' end a variable sequence, wherein said binding site is present in each said member of said array.

6. The method according to claim 1, wherein said enzymatic synthesis is performed using an enzyme.

7. The method according to claim 1, wherein said oligonucleotide primer of step (b) is between 10 and 30 nucleotides in length.

8. The method according to claim 1, wherein said first strand of step (a) comprises DNA.

9. The method according to claim 1, wherein said second strand of step (c) comprises DNA.

10. The method according to claim 1, wherein said first and second strands each comprise from 16 to 60 monomers selected from the group that includes ribonucleotides and deoxyribonucleotides.

11. The method according to claim 1, wherein said solid support is a silica support and said first and second strands each comprise from 16 to 60 monomers selected from the group that includes ribonucleotides and deoxyribonucleotides.

* * * * *

UNITED STATES PATENT AND TRADEMARK OFFICE
CERTIFICATE OF CORRECTION

PATENT NO.   : 6,326,489 B1
DATED        : December 4, 2001
INVENTOR(S)  : George M. Church and Martha L. Bulyk Page 1 of 1

It is certified that error appears in the above-identified patent and that said Letters Patent is hereby corrected as shown below:

Column 1,
Line 3, of the issued patent, after the title kindly insert the following: -- This invention was supported by DOE Grant No. DEFG02-87ER-60565 and the U.S. government has certain rights to the invention. --

Signed and Sealed this

Seventh Day of May, 2002

Attest:

Attesting Officer

JAMES E. ROGAN
Director of the United States Patent and Trademark Office